(12) United States Patent
Yoshizato et al.

(10) Patent No.: US 7,470,550 B2
(45) Date of Patent: Dec. 30, 2008

(54) METHOD OF EVALUATING CELL ACTIVITY

(75) Inventors: Katsutoshi Yoshizato, Higashihiroshima (JP); Hajime Sato, Higashihiroshima (JP); Michihiro Hide, Hiroshima (JP); Tomoko Tsutsui, Higashihiroshima (JP); Hidekatsu Yoneda, Nagoya (JP)

(73) Assignee: Toyo Advanced Technologies Co., Ltd., Hiroshima (JP)

( * ) Notice: Subject to any disclaimer, the term of this patent is extended or adjusted under 35 U.S.C. 154(b) by 0 days.

(21) Appl. No.: 10/500,225

(22) PCT Filed: Dec. 27, 2001

(86) PCT No.: PCT/JP01/11565

§ 371 (c)(1),
(2), (4) Date: Sep. 3, 2004

(87) PCT Pub. No.: WO03/060514

PCT Pub. Date: Jul. 24, 2003

(65) Prior Publication Data

US 2005/0100904 A1 May 12, 2005

(51) Int. Cl.
G01N 33/553 (2006.01)

(52) U.S. Cl. .................. 436/525; 435/7.2; 435/7.21; 435/7.32; 436/164; 436/524; 436/805

(58) Field of Classification Search ............. 435/4, 435/7.1–7.21, 7.23–7.25, 7.32–7.37, 174–176, 435/287.1, 287.9; 436/63, 164, 805; 356/317–319, 356/445

See application file for complete search history.

(56) References Cited

U.S. PATENT DOCUMENTS 5,327,225 A * 7/1994 Bender et al. ............... 356/445
5,965,456 A * 10/1999 Malmqvist et al. .......... 436/514
6,127,129 A * 10/2000 Corn et al. ..................... 435/6
6,387,614 B1 * 5/2002 Cheng et al. .................. 435/4

FOREIGN PATENT DOCUMENTS

| JP | 2000-162124 | 6/2000 |
|---|---|---|
| JP | 2001-194298 | 7/2001 |
| JP | 2001-208755 | 8/2001 |
| JP | 2001-255267 | 9/2001 |

OTHER PUBLICATIONS

Boulla et al. Binding kinetics of soluble ligands to transmembrane proteins: comparing an optical biosensor and dynamic flow cytometry. Cytometry (2000), vol. 40, pp. 76-80.*

Hoffman et al. Binding and selective detection of the secretory N-terminal domain of the alzheimer amyloid precursor protein on cell surfaces. The Journal of Histochemistry & Cytochemistry (1999), vol. 47, No. 3, pp. 373-382.*

Medina et al. Real-time analysis of antibody binding interactions with immobilized *E. coli* O157:H7 cells using the BIAcore. Biotechnology Techniques (1997), vol. 11, No. 3, pp. 173-176.*

* cited by examiner

*Primary Examiner*—Christopher L Chin
(74) *Attorney, Agent, or Firm*—Wenderoth, Lind & Ponack, L.L.P.

(57) ABSTRACT

The invention provides a method for evaluating the physiological activity of an external stimulus on living cells by means of a surface plasma resonance analyzer, which comprises evaluating the physiological activity of the external stimulus on the cells with an indication of a secondary signal appearing after a primary signal upon the exposure of the living cells to the external stimulus. According to the invention, the level of the physiological activity of an external stimulus on living cells can be evaluated accurately.

1 Claim, 4 Drawing Sheets

METHOD OF EVALUATING CELL ACTIVITY

This application is a U.S. National Stage International Application No. PCT/JP01/11565 filed Dec. 27. 2001.

TECHNICAL FIELD

The present invention relates to a method for evaluating cell activity. More particularly, it relates to a method for evaluating the physiological activity of an external stimulus on living cells or a method for screening the living cells responding to an external stimulus using a surface plasmon resonance analyzer (SPR analyzer). The methods can be utilized in an in vitro test of drugs, toxic substances, and the like.

BACKGROUND ART

If the effects of an external stimulus such as ligand binding, environmental change in temperature or pH, mechanical or electrical stimulus, and the like on living cells can be observed in real time in an alive state, it would be possible to measure more accurately the effect of various active substances or physical conditions exerted on the cells, greatly contributing to a rapid diagnosis and determination of a therapeutic strategy in clinical sites. It is accordingly desired to develop an apparatus or diagnostic system for allowing the evaluation of the physiological activity on such cells since there is no device or system available for clinical tests until now.

For example, stimulation of mast cells results in aggregation of high-affinity IgE receptors at the first stage, followed by phosphorylation of α- and β-chains within several seconds. These changes induce association and phosphorylation of a variety of kinase proteins to activate a series of enzymes involved in the intracellular signal transduction such as tyrosine kinase, phospholipase C or G protein, causing a release of a chemical transmitter by infusion of secretory granules to cell membranes after several to several ten minutes. It is known that, simultaneously, a transcription factor is activated, and after a lapse of several to several ten hours, proinflammatory cytokines such as TNFα and IL-4 are synthesized and released.

So far, the dynamic behavior of cellular degranulation has been measured by recovering the supernatant of the reaction medium every time the analysis required to determine the content of the materials such as histamine and cytokines contained therein. In this method, however, it was necessary to recover at least a part of the supernatant of the reaction mixture for measurement and to suspend the reaction simultaneously with the measurement because the reaction condition be easy to change.

In addition, dynamics of the intracellular calcium concentration, pH change, intracellular transfer of a particular protein, and so on, can be analyzed by modification of the cells by loading of a specific fluorescent probe or by transfection with a protein containing a GFP tag. In these methods, however, some preliminary modification of the cells is required. Thus, a problem comes that there is a possibility that the cellular function will be influenced at least by the degree of the modification and in principle the cells used in these tests cannot be turned back to the organisms.

On the other hand, in an SPR (surface plasmon resonance) analyzer, it is possible to conduct measurement of the reaction and binding amount between biomolecules such as proteins as well as a kinetic analysis thereof by observing a change of a resonance angle in real time utilizing the surface plasmon resonance phenomenon. The change of a resonance angle depends on a change of permittivity in the vicinity of a gold film on a sensor. The one end of a protein to be measured for the binding is first immobilized on the gold film. Proteins each has an intrinsic permittivity. In SPR, the binding of a ligand to a protein fixed on the gold film is measured. When the binding of the ligand to the protein occurs, the complex is formed on the gold film and the permittivity will be changed. That is, information on the amount of the binding between biomolecules, kinetic constant of binding, kinetic constant of dissociation, dissociation constant, affinity constant, and the like, can be obtained by following up the permittivity of the surface of the gold film in real time.

An alternative device has been developed in which the amount of a ligand binding to the fixed living cells, kinetic constant of binding, kinetic constant of dissociation, dissociation constant, affinity constant, and the like can be measured in addition to the biomolecules such as proteins.

As mentioned above, an SPR analyzer in which a living cell can be targeted, permits measurement of the change of permittivity during exposure of the cell to an external stimulus. This time, the present inventors have found that the reaction of cells per se caused by an external stimulus makes the permittivity change.

The present application has been filed in view of the above-mentioned situation for the purpose of providing a new method for evaluating accurately the level of the physiological activity of an external stimulus on living cells.

DISCLOSURE OF INVENTION

In order to solve the above-mentioned problems, the present invention provides a method for evaluating a physiological activity of an external stimulus on living cells by means of a surface plasmon resonance analyzer, which comprises evaluating the physiological activity of the external stimulus on the cells with an indication of a secondary signal appearing after a primary signal upon the exposure of the living cells to the external stimulus.

In a preferred embodiment in the invention, wherein the secondary signal is a signal appearing after elimination of the external stimulus.

BEST MODE FOR CARRYING OUT THE INVENTION

Figure 1:
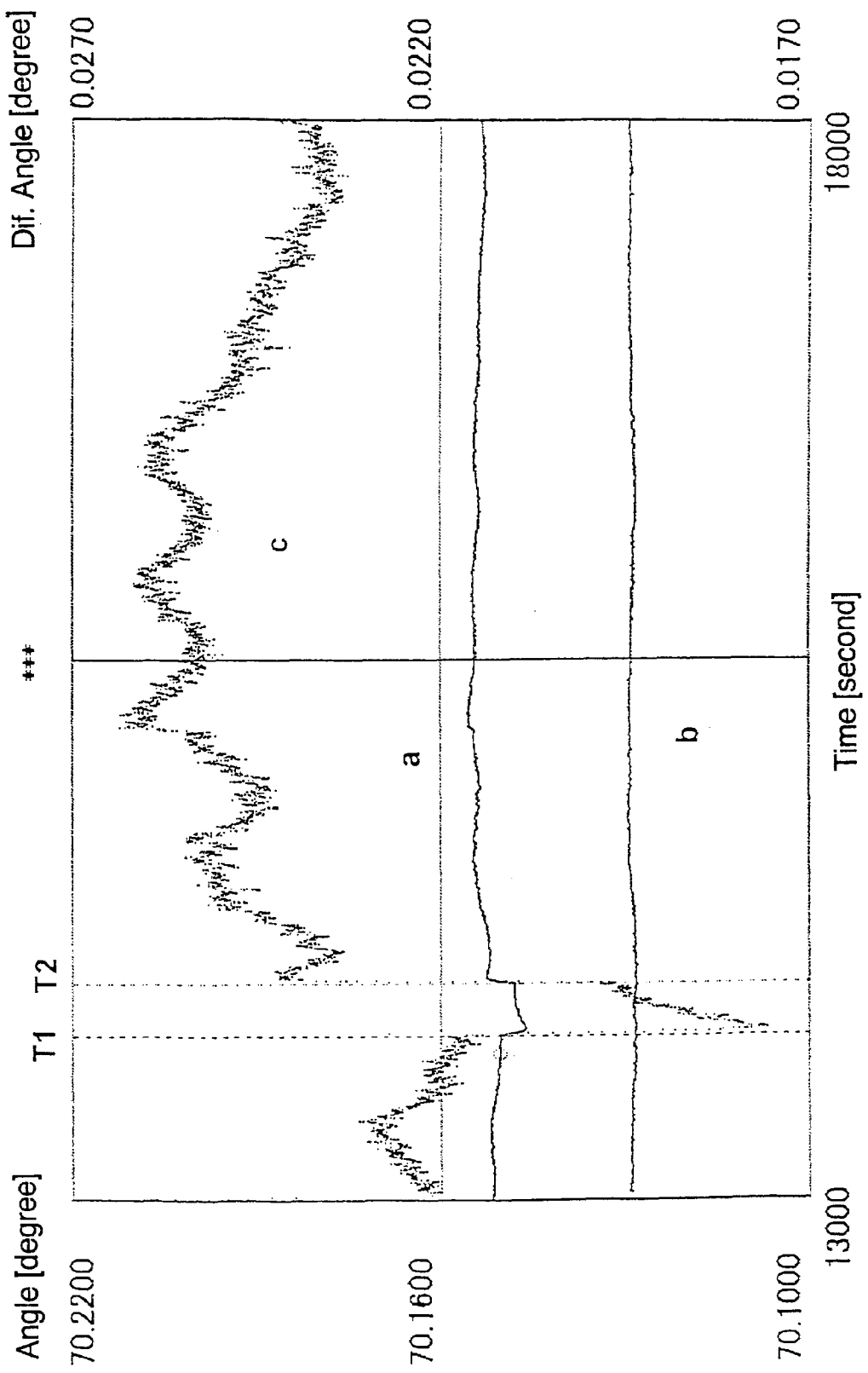
FIG. 1 shows the result of measurement of the IL-2 effect on CTLL2 cells a: IL-2; b: control; and c: the difference between a and b. IL-2 was injected between T1 and T2. The reaction between T1 and T2 indicates the primary signal, and the reaction after T2 the secondary signal.

The term "external stimulus" as used in the method of the invention means all of the stimulation acting on the activity of cells (for example, activation of intracellular signal transduction systems), including ligands acting on the cell surface receptors, environmental changes of temperature or pH, mechanical or electrical stimulation, and the like.

In the method of the invention, cells are immobilized on a analyzer in the same manner as in the usual SPR measurement for vial cells, to which a stimulus as mentioned above is given to determine the signal as a change of permittivity in a conventional procedure. In this procedure, the invention is characterized in that, in addition to a signal observed during the stimulus on the cells (a primary signal), a secondary signal appearing subsequent to the primary signal is measured as an indication for evaluating the cellular activity responding to the external stimulus.

For example, when a ligand is attached to a living cell immobilized on an SPR analyzer, it makes the baseline rise relative to the amount of ligand attached before stabilized (primary signal). When the ligand has a physiological activity to the cell, a further increase or periodical change of the baseline (secondary signal) quite different from the simple binding signal is observed after the primary signal. Such a secondary signal, since it appears only with addition of a ligand of which the physiological activity has been confirmed, is considered as a reflection of some biological reaction caused by the attachment of the ligand to the living cell.

Thus, in the method of the invention, the physiological activity of an external stimulus on cells can be evaluated accurately, and therefore, for example, a change in the cells of a patient caused by antigenic stimulation or administration of a cytokine or drug can be followed up in real time; the result of its analysis can be quickly fed back to a clinical site to utilize it for the decision or prognosis of the therapeutic effect or in the planning of future therapeutic courses. More specifically, it can be utilized in the following clinical diagnosis.

(1) Rapid test for allergic reactions on living cells (blood, biopsy sample, etc.) removed from the organisms, or an induction test with a human body (2) A functional test or determination of whether or not the cells are normal or malignant can rapidly be conducted by stimulating cells of a lesion such as cancerous cells removed in a surgical operation with a cell growth factor and the like. Since the result can be obtained during the operation, the area to be excised can be judged based on the data.

(3) Analysis of the necessary amount of a drug because the amount is different individually. Currently, the difference of the reactivity to a drug among individuals is confirmed by conducting a gene mutation analysis (SNP) in order to realize a so-called tailor-made therapy. According to the method of the invention, the reactivity of individual blood cells (e.g., lymphocytes, basophils, eosinophils, antigen-presenting cells) to a drug can be analyzed, and thus the amount of a drug to be given, which amount is different individually, can be calculated.

(4) Diagnosis of drug allergy: in some rare cases, a certain drug for which the safety has been confirmed in clinical tests in most people may cause a severe allergic reaction. However, when plural kinds of drugs have been administered, it is difficult to identify which is the causative drug. According to the method of the invention, it is possible to identify the causative drug for the allergy based on the analyzed reactivity of the patient's leukocytes to the drug.

(5) The rate of implantation of a fertilized ovum obtained by in vitro fertilization is not so high. In this situation, it is possible to select a fertilized ovum of high implantation rate and return it to the uterus since the cells can be handled in an alive state. Thus, the accuracy of the in vitro fertilization can be enhanced and at the same time a mental and physical burden of a woman who wants artificial insemination can greatly be reduced.

(6) The cellular reaction caused by various substances or by changing physical conditions (for example, aggregation/association of receptor molecules and/or their relative intracellular signal transduction molecules, and their phosphorylation, dephosphorylation, intracellular translocation to or from membranes) is measured. The information is useful in selection of therapeutic agents and judgment of their therapeutic effect.

(7) In culturing animal cells, as we often experience, there is a wide range of variation in lots of serum which is added to a culture medium, resulting in failure to obtain reproducibility of the data. Monitoring of the cellular reaction in the presence of sera by means of SPR permits rapid control of sera

EXAMPLES

The method of the invention will be explained in more detail by the following examples, which are not intended to limit the scope of the invention. In the following examples, SPR-CELLIA (Japan Laser Electronic Co.) was used as an SPR analyzer. The sensor chip for amine coupling was prepared as follows.

In 10 µM solution of 4,4-dithiodibutyric acid in ethanol was immersed a sensor chip and stirred for 30 minutes. Thereafter, the chip was washed with dry ethanol and dried. Water-soluble carbodiimide (25 mg) was dissolved in 1 ml of MilliQ water, and 15mg of N-hydroxysuccinimide in 9 ml of 1,4-dioxane, respectively. Both solutions were mixed immediately before the dried sensor chip was immersed therein and the mixture stirred for 10 minutes. Then, there was added 10 ml of MilliQ water, and the mixture was stirred for 5 minutes. The chip was washed with MilliQ water and preserved in MilliQ water.

Example 1

Reaction of CTLL2 Cells (Suspended Cells) with IL-2

The suspension (30 µl) of CTLL-2 cells ($2 \times 10^5$ cells/ml) in PBS were directly placed onto both of sensor chip-measuring portion and control portion, and the chip was blocked with 50 µl of 1% BSA. The sensor chip was equipped in a flow-cell unit of the SPR analyzer, of which the temperature was set at 37° C. and was perfused with PBS at a flow rate of 15 µl/min. IL-2 (62.5 ng/ml, 60 µl) was injected into the measuring portion, while PBS continuously perfused, and the change of the signal was measured. The portion into which no IL-2 was injected was used as a control.

The result is as shown in FIG. 1. The difference of the signals between the measuring portion and the control portion was obtained, indicating that a characteristic signal appeared at a periodicity of about 10 minutes. This is observed only in living cells. On the other hand, when an agent such as IL-3, bFGF, aFGF or pleiotrophin, which does not bind to CTLL-2 cells, was added, no signal was observed.

This indicates that the living cells binding to a ligand generated some events, which were captured by SPR.

Example 2

Reaction of Papilla Cells (Mesenchyme Cells) with bFGF

Papilla cells were removed from a petri dish with 0.02% EDTA and suspended in a DMEM10 culture medium. The cells ($2\times10^5$ cells/ml, 400 μl) were immobilized on a sensor chip in the same manner as in Example 1.

PBS was perfused at a flow rate of 15 μl/min at a fixed temperature of 37° C.; 1 μg/ml of bFGF alone was injected into a control portion, and 60 μl of μg/ml bFGF+50 μM phosphorylation inhibitor (SU4984) into a measuring portion; after a lapse of 42 seconds the circuit was closed and the change of signals was measured.

Figure 2:
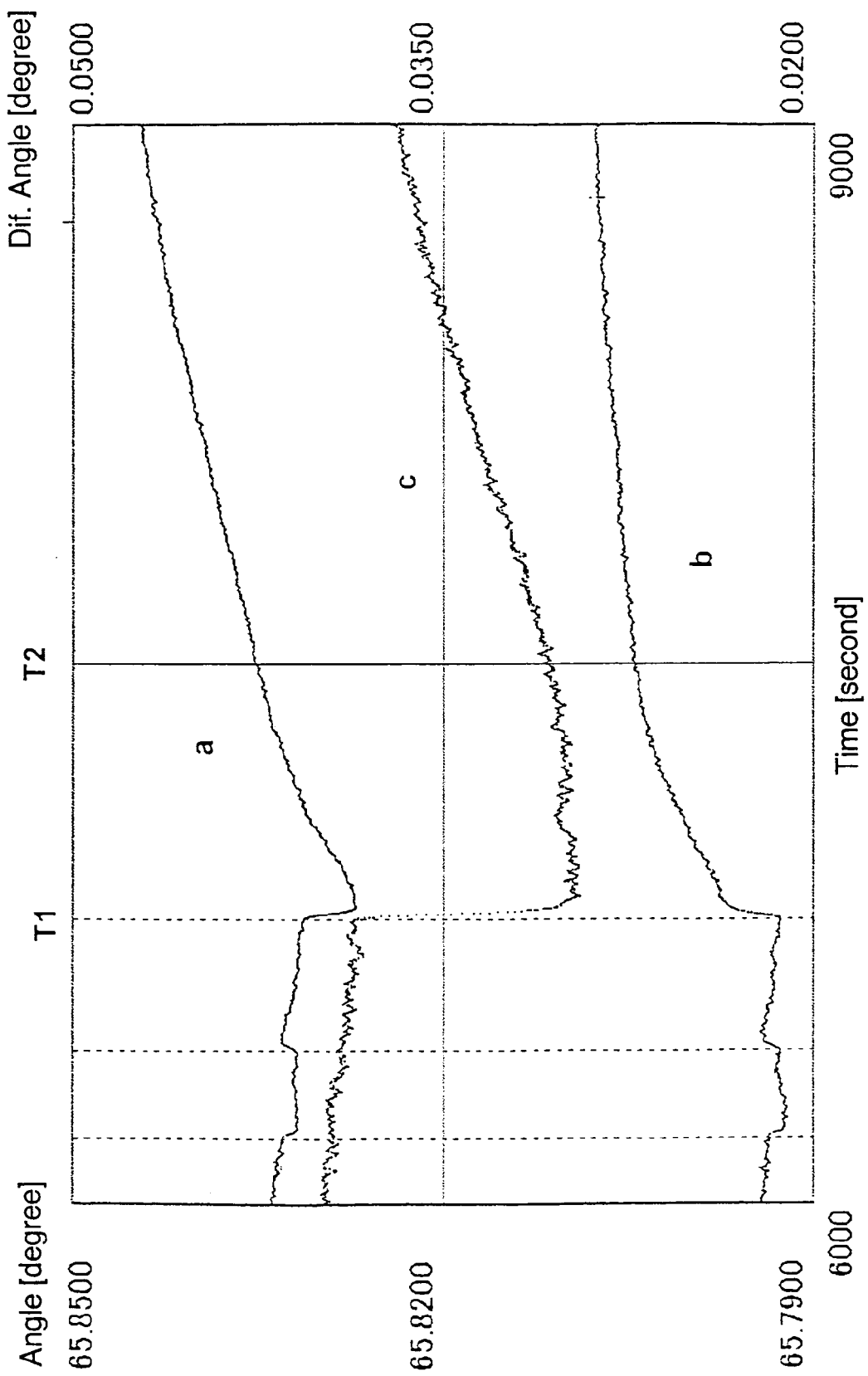
FIG. 2 shows the result of measurement of the bFGF effect on papilla cells. a: bFGF; b: bFGF+inhibitor, c: the difference between a and b. At the point of T1, bFGF (and an inhibitor) was injected. The reaction between T1 and T2 indicates the primary signal, and the reaction after T2 the secondary signal.
Figure 3:
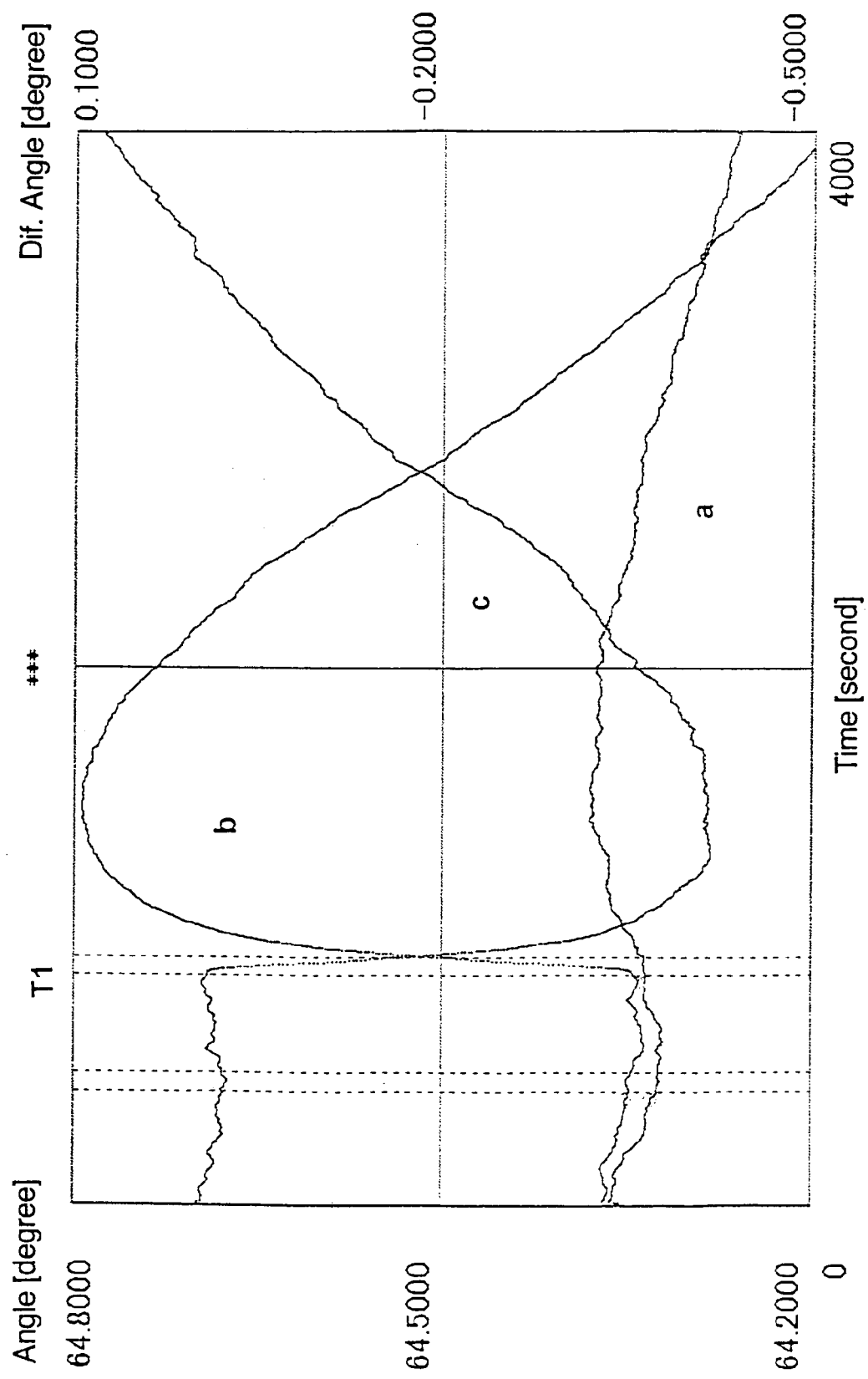
FIG. 3 shows the result of measurement of the antigenic effect on mast cells. a: DNP-HSA stimulation on IgE unsensitized cells; b: DNP-HSA stimulation on IgE sensitized cells; c: the difference between a and b. At the point of T1, DNP-HAS was injected. The reaction after T1 indicates the secondary signal. The secondary signal appeared so strongly that no primary signal was recorded.

The result is as shown in FIG. 2. From 10 minutes after the injection, the signal from the SU4984-treated portion became plateau, while the signal from bFGF alone ascended continuously. This indicates that the signal transduction caused by the binding of bFGF was suppressed by the phosphorylation inhibitor.

Example 3

Reaction of Mast Cells on an Antigen

Mast cells ($2\times10^5$ cells/ml, 70 μl) were immobilized on a sensor chip in the same manner as in Example 1. IgE was added to a measuring portion, and incubated in a $CO_2$ incubator at 37° C. overnight. The chip was set on an SPR analyzer, and a running buffer (PIPES buffer, pH 7.2) was perfused at a flow rate of 15 μl/min at a fixed temperature of 37° C. Then, 60 μl of 100 ng/ml DNP-HSA (dinitrophenyl-human serum albumin) or 10 μg/ml DNP-lysine was injected, while a running buffer was perfused continuously, and the change of signal was measured. The composition of PIPES (piperaine-N,N'-bis[2-ethane-sulfonic acid]; 1,4-piperzine-diethane-sulfonic acid) buffer is as shown in Table 1.

TABLE 1

| NaCl | 119 (mM) |
|------|----------|
| KCl  | 5        |

TABLE 1-continued

| PIPES      | 25  |
|------------|-----|
| Glucose    | 5.6 |
| MgCl2 6H2O | 0.4 |
| NaOH       | 40  |
| CaCl2      | 1   |

Figure 4:
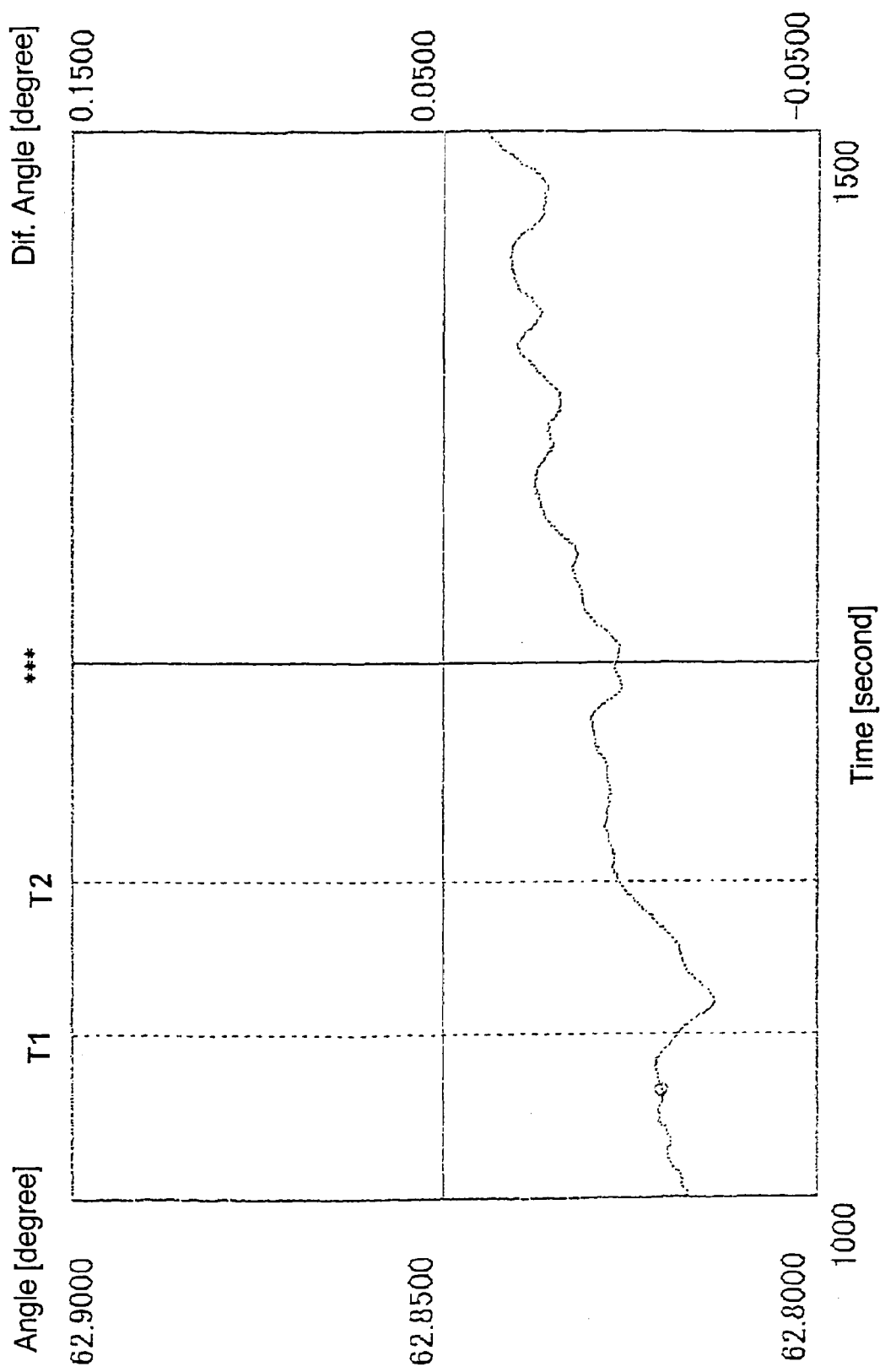
FIG. 4 shows the result of measurement of the DNP-lysine effect on mast cells. At the point of T1, DNP-lysine was injected. The reaction between T1 and T2 indicates the primary signal.

The result is as shown in Table 3. When DNP-HSA was injected, a strong signal was observed in the IgE sensitized mast cells, reflecting the activation by a specific antigen-antibody reaction, but no characteristic change in the unsensitized mast cells. When DNP-lysine which binds to but does not activate the cells was injected, the primary signal generated by the binding of DNP-lysine was observed, but no secondary signal observed (FIG. 4). From these results, it was confirmed that the activation of cells could be measured rapidly according to the method of the invention.

Industrial Applicability

According to the invention, as described above in detail, it becomes possible to evaluate conveniently and accurately the presence or absence or the level of the cellular activity induced by external stimuli. For example, it is possible to judge the effect of drugs or allergens on cells in an alive state taken out from patients; thus, clinically useful information can be obtained. In addition, the cells used in diagnosis can be used in replantation, and accordingly the invention can be applied to in vitro fertilization as well as to cell implantation or an ex vivo type gene therapy.

The invention claimed is:

1. A method for evaluating the biological activity of a specific binding substance on living cells by means of a surface plasmon resonance analyzer, which comprises:
   immobilizing the living cells on a surface plasmon resonance analyzer;
   applying a flow of the specific binding substance to the living cells;
   continuously measuring a primary signal, which appears upon application of the flow, and measuring a secondary signal, which appears after elimination of the flow; and
   evaluating the biological activity of the specific binding substance on the cells by indication of the secondary signal, which comprises a further increase or periodical change from the signal level measured the end of the primary signal.

* * * * *